United States Patent
Rama Rao et al.

(10) Patent No.: US 10,842,348 B2
(45) Date of Patent: Nov. 24, 2020

(54) IMPLANTABLE COMMUNICATION SYSTEM STARTER SYSTEM AND METHODS

(71) Applicants: OLYMPUS CORPORATION, Tokyo (JP); Kishore Rama Rao, San Diego, CA (US)

(72) Inventors: Kishore Rama Rao, San Diego, CA (US); Kim Heng, San Diego, CA (US)

(73) Assignee: OLYMPUS CORPORATION, Tokyo (JP)

(*) Notice: Subject to any disclaimer, the term of this patent is extended or adjusted under 35 U.S.C. 154(b) by 123 days.

(21) Appl. No.: 16/090,134

(22) PCT Filed: Mar. 29, 2016

(86) PCT No.: PCT/IB2016/000479
§ 371 (c)(1),
(2) Date: Sep. 28, 2018

(87) PCT Pub. No.: WO2017/168188
PCT Pub. Date: Oct. 5, 2017

(65) Prior Publication Data
US 2019/0110660 A1    Apr. 18, 2019

(51) Int. Cl.
*A61B 1/00*    (2006.01)
*H03K 19/00*    (2006.01)
(Continued)

(52) U.S. Cl.
CPC .......... *A61B 1/00036* (2013.01); *A61B 1/041* (2013.01); *H03K 19/0016* (2013.01);
(Continued)

(58) Field of Classification Search
CPC ............... A61B 1/00036; A61B 1/041; H03K 19/0016; H04W 52/0229; H04W 52/028
(Continued)

(56) References Cited

U.S. PATENT DOCUMENTS

| 5,682,603 A | 10/1997 | Sano |
| 7,593,455 B2 | 9/2009 | Son |

(Continued)

FOREIGN PATENT DOCUMENTS

| EP | 2858430 | 4/2015 | |
| EP | 2858430 A1 * | 4/2015 | ........ H04W 52/0206 |
| JP | 2013-146437 | 8/2013 | |

OTHER PUBLICATIONS

International Search Report and Written Opinion for PCT/IB2016/000479 dated Feb. 3, 2017, 25 pages.
(Continued)

*Primary Examiner* — Ayodeji O Ayotunde
(74) *Attorney, Agent, or Firm* — Sheppard, Mullin, Richter & Hampton LLP

(57) ABSTRACT

A starter circuit for an electronic device includes a rectifier circuit having an input coupled to an antenna; a Schmidt trigger coupled to the rectifier circuit; a pulse timer circuit coupled to receive pulses from the Schmidt trigger and configured to measure pulse characteristics to determine whether the pulses are part of a valid startup sequence and to generate a reset signal if the pulses are not part of a valid startup sequence; and a counter having first and second inputs coupled to outputs of the pulse timer circuit, the counter configured to output a signal to initiate power-on of a component of the electronic device a when its count value reaches a predetermined value.

24 Claims, 8 Drawing Sheets

(51) Int. Cl.
*H04W 52/02* (2009.01)
*A61B 1/04* (2006.01)
*A61N 1/08* (2006.01)
*A61N 1/372* (2006.01)
*H04B 1/16* (2006.01)

(52) U.S. Cl.
CPC ..... *H04W 52/028* (2013.01); *H04W 52/0229* (2013.01); *A61N 1/08* (2013.01); *A61N 1/37276* (2013.01); *H04B 1/1615* (2013.01); *Y02D 30/70* (2020.08)

(58) Field of Classification Search
USPC .......................................................... 455/73
See application file for complete search history.

(56) References Cited

U.S. PATENT DOCUMENTS

| | | |
|---|---|---|
| 7,668,596 B2 | 2/2010 | Von Arx |
| 8,802,183 B2 | 8/2014 | Frank |
| 8,824,345 B2 | 9/2014 | Kim |
| 8,938,304 B2 | 1/2015 | Zierhofer |
| 9,161,707 B2 | 10/2015 | Hafezi |
| 9,184,875 B2 | 11/2015 | Sicurello |
| 2006/0270381 A1 | 11/2006 | Park |
| 2009/0245454 A1 | 10/2009 | Matsuno |
| 2010/0216523 A1* | 8/2010 | Sebastiano ........ H04W 52/0229 455/574 |
| 2015/0087255 A1 | 3/2015 | Wentzloff |

OTHER PUBLICATIONS

Office Action dated Jan. 28, 2020 for Japanese Application No. 2018-550504.

* cited by examiner

IMPLANTABLE COMMUNICATION SYSTEM STARTER SYSTEM AND METHODS

CROSS-REFERENCE TO RELATED PATENT APPLICATIONS

This application is a U.S. national stage entry under 35 U.S.C. 371 of International Application No. PCT/IB2016/000479, filed on Mar. 29, 2016, which is incorporated herein by reference in its entirety.

TECHNICAL FIELD

The disclosed technology relates generally to power control, and more particularly, some embodiments relate to a starter for an implantable communication system.

DESCRIPTION OF THE RELATED ART

As portable electronic devices have gained popularity, battery life, and hence power control has become an important consideration in device design. Numerous electronic devices, especially wireless and portable devices have been designed to prolong battery life. Implantable medical devices are no exception. Indeed, low power consumption is a very important feature of implantable circuits to allow the device to achieve a long operating time and reduce the space required for the battery or other power supply.

Subthreshold operation is one technique used to reduce the power consumed by electronic devices. Duty-cycling is another technique whereby the device is in a 'sleep mode' when not processing or communicating, and wakes up according to a MAC protocol for a relatively short period of time. The leakage current during the sleep-mode is hence a very important factor in the overall power consumption of the device. Sleep mode can also be used not only between active communication windows, but it can also be used for the period of time between device assembly and the first use of the device. Once the battery is connected, a power-on-reset (POR) circuitry detects the presence of stable voltage from the battery/power source and generates a reset pulse to reset the digital logic. Then the device may go into a low power sleep mode where a low frequency clock and minimal power management unit (PMU) circuitry is on. The device 'wakes-up' at specified intervals and listens for a 'wake-up' or 'activate' signal. When such a signal exists, the chip is powered on to transmit or receive data.

Manual battery connection may not be available in many applications, as is the case with hermetically sealed components. Because the battery is always connected in hermetically sealed applications, the leakage current is much more important, especially where the device remains on a shelf for a long period before being used. Magnetic/reed switches have been used as a startup circuit to break the power connection until the device is ready to be activated. However, the magnetic switch is bulky and adds additional components to the device, which is undesirable for implantable/ingestible devices. Additionally the presence of a magnetic switch may prevent or interfere with the use of other diagnostics that rely on a magnetic field or with navigation of an ingestible component using a magnetic field.

United States Patent Application Publication No. 2006/0270381 A1 employs a wireless receiver that is enabled upon receiving a specific, predetermined identification signal to receive data, and uses circuitry to discriminate the identification signal. This conventional solution uses two wake up signals, the $1^{st}$ of which is generated when a wireless signal is received in a predetermined frequency band. The $2^{nd}$ of which is generated by an ID detector that decodes the received signal and determines whether the decoded signal is a predetermined identification signal.

BRIEF SUMMARY OF EMBODIMENTS

According to various embodiments of the disclosed technology, startup circuitry is provided to reduce battery drain and therefore prolong the shelf life of an energy-storage-unit for the device. In various embodiments, the startup circuit utilizes the device's existing transceiver antenna to couple a start signal while adding very little circuit complexity to the transceiver. The circuit can be configured such that few or no additional components are added to the device and hence not materially increase the circuit board area. This feature can be important for implantable or ingestible components.

According to an embodiment of the disclosed technology a radio communication device includes an antenna; a transceiver including an input coupled to receive signals from the antenna, the transceiver comprising an active mode and a sleep mode; an AC starter circuit including an input coupled to receive signals from the antenna and an output coupled to the transceiver, the AC starter circuit comprising a rectifier circuit coupled to receive the signals from the antenna and configured to generate a rectified radio signal only when a power level of the received signals is equal to or greater than a first predetermined power level; wherein the AC starter circuit sends an activation signal to the transceiver only when: (i) the power level of the received signal is equal to or greater than the first predetermined power level, which is greater than a power level of communication signals received by the transceiver, and (ii) the received signals include a startup sequence that is a predetermined startup sequence indicating that the transceiver is to switch from the sleep mode to the active mode; and wherein the AC starter circuit does not send the activation signal to the transceiver when the power level of the received signals is not equal to or greater than the first predetermined power level or when the startup sequence is not the predetermined startup sequence. Further wherein the transceiver switches its operation mode from the sleep mode to the active mode when the transceiver in the sleep mode receives the activation signal from the AC starter circuit. In various embodiments, the transceiver in the active mode decodes a radio signal received by the antenna, when a power level of the radio signal is equal to or greater than a second predetermined power level; and the AC starter circuit consumes a leakage current less than a leakage current which the transceiver consumes in the active mode. In some embodiments, the second predetermined power level is within a dynamic range in which the transceiver is operable; and the first predetermined power level is more than double the second predetermined power level. The may be AC starter circuit is configured to send a shutdown signal to the transceiver to cause the transceiver to switch to the sleep mode.

In further embodiments, the AC starter circuit may be configured to send the shutdown signal to the transceiver only when: (i) the power level of the received signal is equal to or greater than the predetermined power level, and (ii) the received signals include a shutdown sequence that is a predetermined shutdown sequence indicating that the transceiver is to switch from the active mode to the sleep mode. The shutdown sequence may be different from or the same as the startup sequence.

In other embodiments, the AC starter circuit may include an input coupled to receive signals from the antenna and an output coupled to the transceiver, the AC starter circuit comprising a rectifier circuit coupled to receive the signals from the antenna and configured to generate a rectified radio signal only when a power level of the received signals is equal to or greater than a first predetermined power level; wherein the AC starter circuit sends A/D activation signal to the transceiver only when: (i) the power level of the received signal is equal to or greater than the first predetermined power level, which is greater than a power level of communication signals received by the transceiver, and (ii) the received signals include a shutdown sequence that is a predetermined shutdown sequence indicating that the transceiver is to switch from the active mode to the sleep mode; and wherein the AC starter circuit does not send the deactivation signal to the transceiver when the power level of the received signals is not equal to or greater than the first predetermined power level or when the shutdown sequence is not the predetermined shutdown sequence; further wherein the transceiver switches its operational mode from the active mode to the sleep mode when the transceiver in the active mode receives the deactivation signal from the AC starter circuit.

In other embodiments, A wireless ingestible endoscopy system, includes an endoscopy data terminal; and a wireless ingestible endoscope. The wireless ingestible endoscope can include an image sensor; a communication transceiver coupled to receive images from the image sensor and configured to send images to the endoscopy data terminal; and a starter circuit. The starter circuit may include a rectifier circuit comprising an input coupled to an antenna; a Schmidt trigger comprising an input coupled to receive a rectified signal from the rectifier circuit; a pulse timer circuit coupled to receive pulses from the Schmidt trigger and configured to measure pulse characteristics to determine whether the pulses are part of a valid startup sequence and to generate a reset signal if the pulses are not part of a valid startup sequence; a counter having first and second inputs coupled to outputs of the pulse timer circuit, the counter configured to output a signal to initiate power on of the transceiver when the counter's count value reaches a predetermined value.

The system can further include an external antenna, and wherein the images are sent from the communication transceiver wireless ingestible endoscope to the endoscopy data terminal via the external antennas.

In some embodiments, measuring pulse characteristics to determine whether the pulses are part of a valid startup sequence comprises measuring timing parameters of the detected pulses to determine whether the pulses meet predetermined timing parameter characteristics. The timing parameters may include a pulse width and a period of the detected pulses in the received signal.

The rectifier circuit may be configured to output the rectifying signal only if a power level of a signal received by the rectifier circuit from the antenna is equal to or greater than a predetermined power level. In various embodiments, the starter circuit sends the signal to initiate power-on of a component of the electronic device only when: (i) the power level of a signal received by the rectifier circuit is equal to or greater than the first predetermined power level, which is greater than a power level of communication signals received by the transceiver, and (ii) the received signals include a startup sequence that is a predetermined startup sequence indicating that the transceiver is to switch from a sleep mode to an active mode. The rectifier circuit may comprise a power detector.

The starter circuit may be configured to send a deactivation signal to the transceiver to cause the transceiver to switch to a sleep mode when: (i) the power level of the received signal is equal to or greater than the predetermined power level, and (ii) the received signals include a shutdown sequence that is a predetermined shutdown sequence indicating that the transceiver is to switch from the active mode to the sleep mode.

In various embodiments, the starter circuit consumes a leakage current in a sleep mode that is less than a leakage current a component of the electronic device consumes in an active mode.

In other embodiments, a method for initiating power-on of a wireless electronic device, includes: receiving a signal from an antenna; detecting pulses in the signal using a Schmidt trigger; measuring characteristics of the detected pulses to determine whether the pulses are valid pulses of a startup sequence; and outputting a signal to initiate power of a transceiver of the electronic device when a predetermined quantity of valid pulses are received. Measuring characteristics of the detected pulses to determine whether the pulses are valid pulses of a startup sequence may include measuring timing parameters of the detected pulses. The method may further include counting detected valid pulses using a counter to determine whether the predetermined quantity of valid pulses are received. The method may further generate a reset signal if the pulses are not part of a valid startup sequence, wherein the reset signal resets the counter.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

Embodiments of the technology disclosed herein are directed toward devices and methods for providing a starter signal to electronic devices. More particularly, embodiments of the technology disclosed herein relate to a starter circuit provided to allow the electronic device to be in a sleep or power-down mode when the electronic device is not in use. This can be, for example, while the device is in shipment or in storage (e.g. in inventory) prior to its intended use. The starter circuit can be configured to detect a startup signal received from an external device, and energize the electronic device when the startup signal is received and verified. The starter circuit can also be used to detect a shutdown signal received from an external device, and to transition the electronic device to a sleep mode when the shutdown signal is received and verified. The starter circuit can be configured to remain in a low power mode, while listening to detect the startup signal. The startup and shutdown signals can be, for example, specific pulse sequences meeting predetermined patterns. In some embodiments, the startup and shutdown sequences can be the same sequences, or they can be different sequences (e.g., pulse trains with different parameters).

Figure 1:
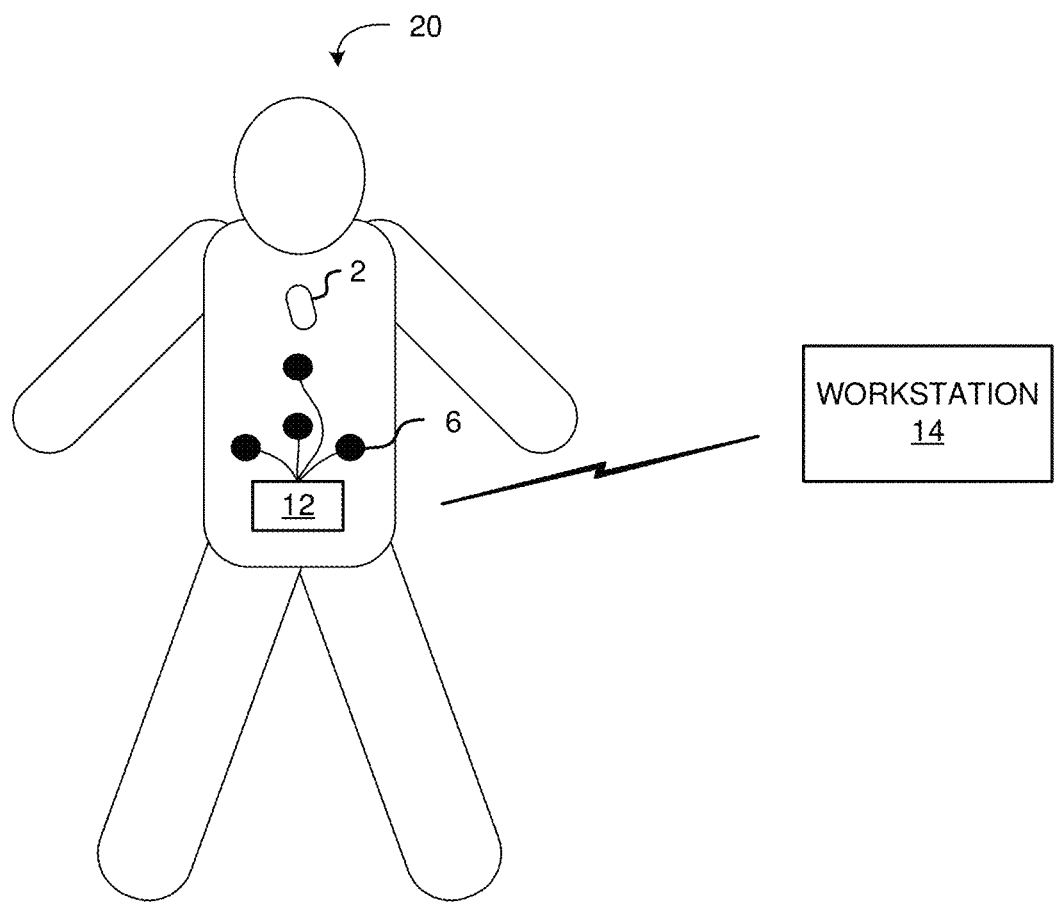
FIG. 1 is a diagram illustrating an example WCE system in accordance with one embodiment of the technology described herein.

Before describing embodiments of the starter circuit in detail, it is useful to describe an example application with which this disclosed technology may be implemented in various embodiments. One such example application is that of an ingestible endoscope, such as a wireless capsule endoscope. Wireless capsule endoscopy (WCE) has gained increasing popularity for providing diagnostic technology to inspect the gastrointestinal (GI) tract. FIG. 1 is a diagram illustrating an example WCE system in accordance with one embodiment of the technology described herein. This example system includes a capsule endoscope 2, a plurality of external antennas 6 (external to the body of the subject), a wearable data recorder 12, and a workstation 14. Capsule endoscope 2 is packaged in a small capsule that is ingestible by a human subject 20. Capsule endoscope 2 includes an image sensor to capture images of the subject's GI tract and a transceiver to transmit those images wirelessly outside the body for analysis. An example of a capsule endoscope 2 is described further below with reference to FIG. 2.

In operation, capsule endoscope 2 is powered on (e.g., using the starter circuit according to various embodiments described herein) and swallowed by the human subject 20. Cameras onboard capsule endoscope 2 begin gathering images and transmitting those images via a wireless transmitter (which may be part of a wireless transceiver) to a receiver outside of the human body. In this example, a plurality of external antennas 6 are configured to receive the signals transmitted by the transmitter in capsule endoscope 2, and send those signals to an endoscopy data terminal, which can comprise the wearable recording device 12 or workstation 14 or a combination of wearable recording device 12 and workstation 14.

In some embodiments, wearable recording device 12 is configured to store the image data captured and transmitted by capsule endoscope 2 without further processing and analysis. In other embodiments, wearable recording device 12 can also include the capability to perform image and data analysis as well. Wearable recording device 12 can include, for example, a disk drive or solid state memory to capture and store the image data sent from the capsule endoscope 2. It can also include a hard wired or wireless communications interface to allow communication of the received image data to workstation 14.

In this example, wearable recording device 12 downloads the stored image data to a workstation 14 for further processing (if any) and analysis. A physician or other health care practitioner can inspect the images on workstation 14 and evaluate the patient's condition accordingly. The system can be configured such that wearable recording device 12 downloads the stored image data to workstation 14 over a hard wired or wireless communication link when the patient returns the recording device to the physician's office. In other embodiments, wearable recording device 12 can remotely transfer the data to workstation 14 such as, for example, via a cellular or other remote connection. In further embodiments, data can be sent from the capsule endoscope to the workstation 14 without passing through the data recording device.

The system illustrated in FIG. 1 is configured to allow the human subject 22 ingest the capsule endoscope 2 and go about his or her business outside of the health care facility while images are transferred to and captured by wearable recording device 12. In other applications, the system may be configured to capture data for analysis while the patient remains in the health care facility.

Figure 2:
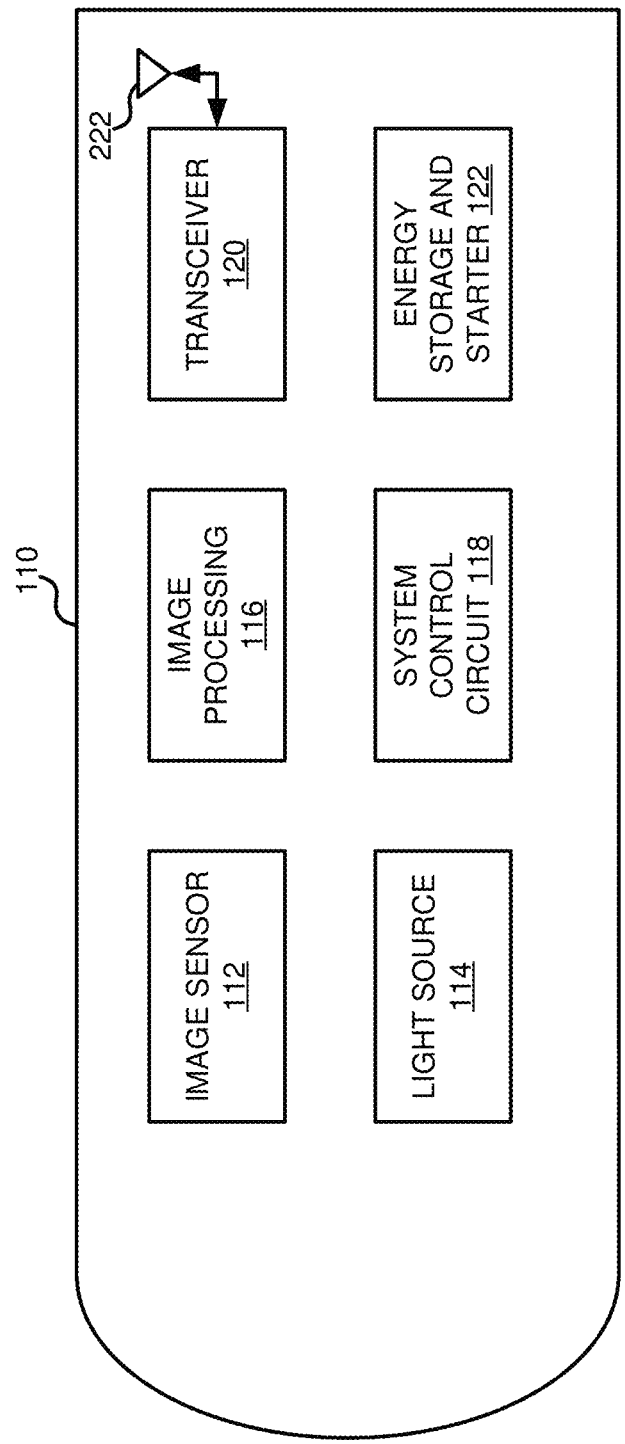
FIG. 2 is a diagram illustrating an example conceptual architecture of an endoscopic capsule with which the disclosed starter circuit may be implemented.

FIG. 2 is a diagram illustrating an example conceptual architecture of an endoscopic capsule with which the disclosed starter circuit may be implemented. As seen in FIG. 2, this example ingestible endoscope includes an image sensor 112, a light source 114, an image processing system 116, a controller 118, a wireless transceiver 120, and an energy storage device 122. These components are contained in a sealed container 110.

Although any of a number of different image sensor technologies can be used, some applications use a solid-state image sensor such as a CMOS or CCD image sensor. One or more light emitting diodes can be provided as the light source 114 and a lens (not pictured) for capturing the in-vivo scene and focusing it on the image sensor 112. Images captured by image sensor 112 are provided to image processing system 116 for on-board board processing. In various applications, on-board processing may be limited to conserve power and limit processor requirements. In further embodiments, image processing 116 can be omitted and the output of the image sensor directly transmitted to the external receiver via transceiver 120.

The images are provided to transceiver 120 for transmission to an external receiver. Transceiver 120 can be implemented, for example, as an ASIC or other circuitry configured to wirelessly transmit and receive data via an antenna (not shown in FIG. 1) to and from external devices such as data recorder 12 or workstation 14. Various other components of the endoscopic capsule can also be implemented as part of the ASIC. For example, circuitry such as image processing circuitry, controller 118 and drivers for light source 114 can be implemented in the same ASIC as transceiver 120.

A separate controller 118 is shown in this example and may also be provided to control the operation of the endoscopic capsule. In some applications, however, a controller 118 is not necessary as the device can be configured upon power up to begin capturing and transmitting images.

Energy storage and starter 122 are also included. The energy storage device provides power to the various components of the wireless endoscope. The energy storage device can be implemented, for example, using a battery, capacitor, or other energy storage device capable of storing energy and providing power to the components. A starter can be included to power up the circuitry of the ingestible endoscope prior to usage. This can allow the circuitry to remain powered off until such time, thereby minimizing the leakage current from the power source.

Having thus described an example application with which the disclosed technology can be implemented, various embodiments of a starter circuit are now described. Although these embodiments may be described in terms of this example application, one of ordinary skill in the art will understand how the disclosed technology can be implemented in other applications with other devices besides capsule endoscopes.

In various embodiments, starter circuitry is provided to allow the device to be in a sleep or power-down mode when the device is not in use. This can be, for example, while the device is in shipment or in storage (e.g. in inventory) prior to its intended use. The starter circuitry can be configured to detect a startup signal received from an external device, and energize the endoscope when the startup signal is received and verified. The starter circuitry can be configured to remain in a low power mode (e.g., in a sub-threshold mode) while listening to detect the startup signal. The startup signal can be, for example, the specific pulse train that is used to trigger the startup signal.

Figure 3:
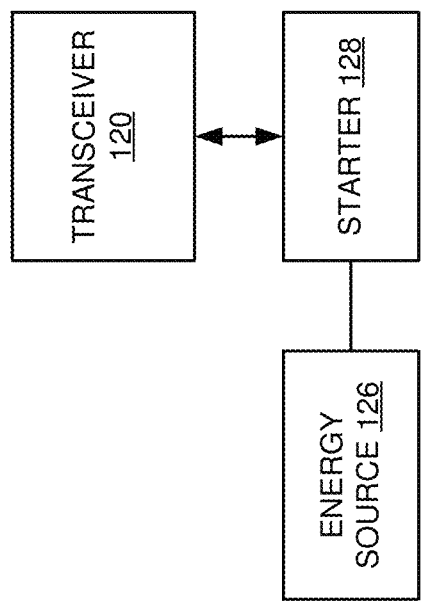
FIG. 3 is an example conceptual block diagram of a starter circuit in conjunction with a device transceiver.

FIG. 3 is an example conceptual block diagram of a starter circuit in conjunction with a device transceiver. As seen in FIG. 3, this example includes starter circuit 128 coupled to an energy source 126 (e.g. a battery) and also coupled to transceiver 120. Initially, transceiver 120 and the image sensor (in addition to other components, if any) are powered down and the battery is only supplying power to the starter circuit. Accordingly, the leakage current is determined solely or substantially solely by the starter circuit. When the starter circuit 128 is activated, it can activate transceiver 120 and power on the device. Likewise, it can be used to transition the device to a sleep mode as well.

Figure 4:
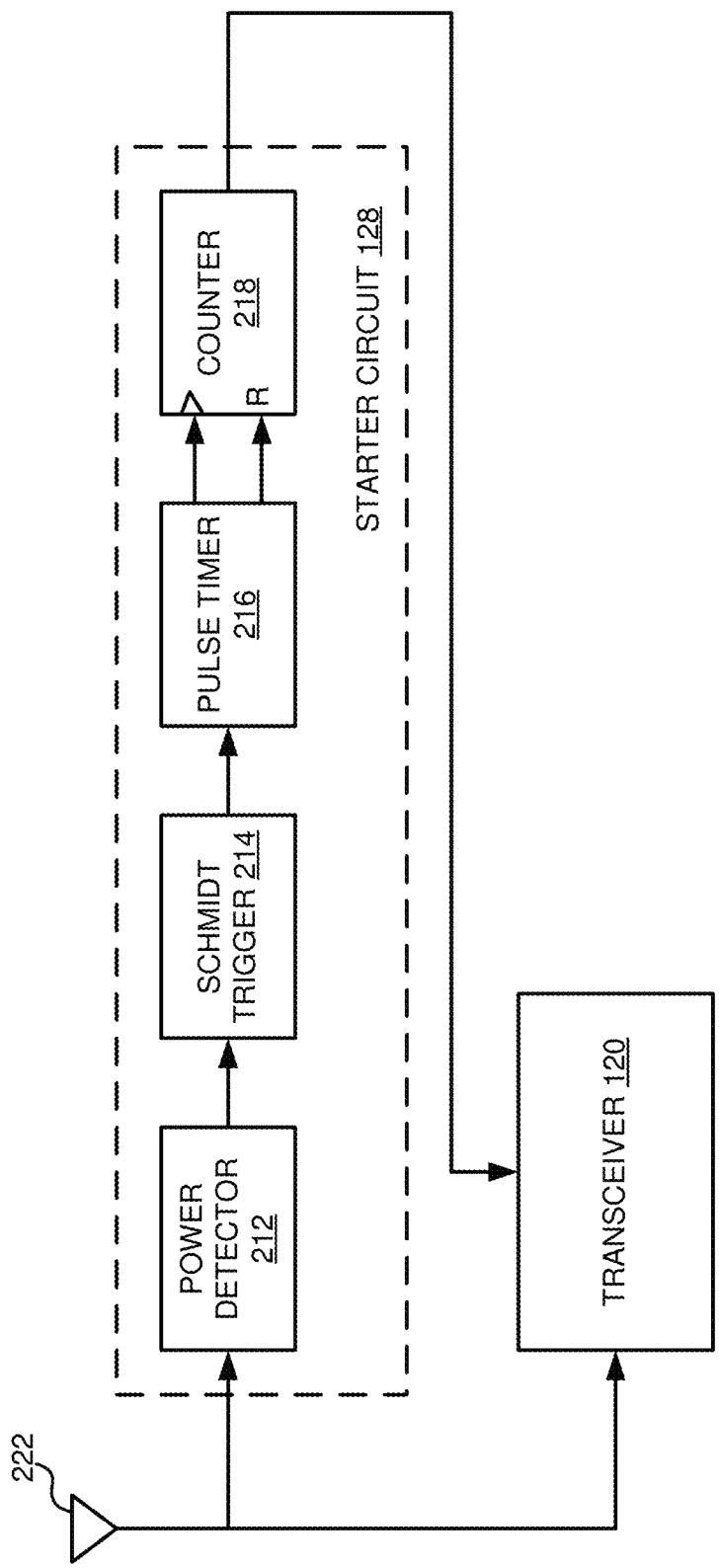
FIG. 4 is a diagram illustrating an example architecture for a starter circuit in accordance with one embodiment of the technology described herein.
Figure 5:
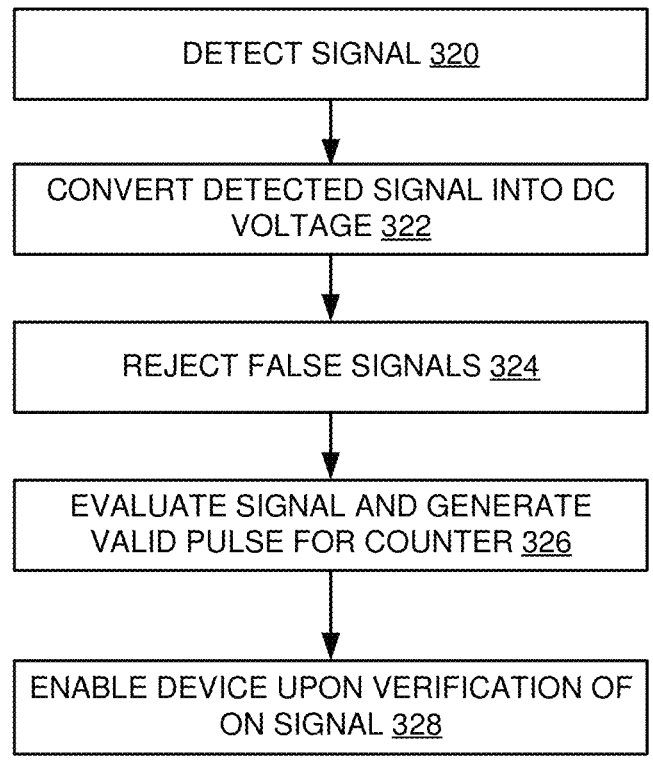
FIG. 5 is a diagram illustrating an example process for operation of starter circuitry 128 in accordance with one embodiment of the technology described herein.

FIG. 4 is a diagram illustrating an example architecture for a starter circuit in accordance with one embodiment of the technology described herein. FIG. 5 is a diagram illustrating an example process for operation of starter circuitry 128 in accordance with one embodiment of the technology described herein. Referring now to FIGS. 4 and 5, this example includes a power detector circuit 212, a Schmidt trigger 214, a pulse timer circuit 216, and a counter circuit 220. Starter circuit 128 includes an input that is coupled to receive (directly or indirectly) signals from antenna 222. In this example, antenna 222 is the same antenna used by transceiver 120 to transmit and receive electromagnetic signals to communicate with external devices such as data recorder 12 or workstation 14. Accordingly, in such a configuration, an additional antenna is not required for the starter circuit 128, thus conserving volume and weight of the electronic device.

At operation 320, power detector circuit 212 receives and detects a signal received by antenna 222. Power detector circuit 212 can be configured to include a squarer circuit followed by a passive low-pass filter. In some embodiments, power detector circuit 212 can be implemented as a rectifier circuit. For example, a peak detector can be implemented using a diode rectifier circuit such as, for example, a half-wave rectifier, with a diode and capacitor connected in series, to output a voltage level corresponding to the peak value of the received signal. Accordingly, at operation 322, power detector circuit 212 produces a DC voltage proportional to the input power at its output. In various embodiments, the power level (e.g., peak power level) needed for the received signal to trigger the rectifier circuit to produce a DC output voltage is a power level that is greater than the signal level used for communications by the electronic device. In some embodiments, this power level can be described as being greater than the operable dynamic range of the devices transceiver. For example, the power level required for this threshold can be double the operable dynamic range of the transceiver. In other embodiments, the power level required for this threshold can be three, four or five times the operable dynamic range of the transceiver.

At operation 324, the signal output by power detector circuit 212 is provided to a Schmidt trigger 214, which minimizes jitter when the power levels are close to the level at which the wake-up current is activated. Schmidt trigger 214 can be used to avoid false triggering and square up an otherwise noisy signal into pulses. The Schmidt trigger provides at its output the pulses to pulse timer 216. At operation 326, pulse timer circuit 216 evaluates a pulse width of the received signals from Schmidt trigger 214 and generates a valid output pulse only if the pulse width of the receive signal is within a defined specification. For example, in one embodiment, pulse timer 216 can be configured to generate output pulses only when the input signal corresponds to a predetermined pattern of pulse width and duration. An example of this is described below with reference to FIG. 6.

Additionally, the pulse timer 216 can be configured to generate a reset pulse for the counter 218 when the timing for any of the pulse train parameters is outside the accepted range (i.e., when the predetermined pattern is not detected). That is, the reset signal is generated if the pulse characteristics do not satisfy the requirements for a valid startup sequence. Accordingly, the starter circuit is activated only when the predetermined startup sequence is present at the antenna, which can provide a measure of security against accidental or malicious triggering of the startup circuit.

At operation 328, counter circuit 218 receives the pulses from pulse timer 216 and counts the number of pulses since the last reset signal. If the correct number of valid pulses is reached before the next reset, counter circuit 218 triggers an output startup signal. This activation signal initiates power-on of a component of the electronic device when the count value reaches a predetermined value. For example, the startup signal can be used for enabling, or powering on, the transceiver, or for powering on other appropriate component(s) in the electronic device.

Although primarily described above as generating an activation or startup signal to transition the electronic device into an active mode, the same starter circuit can be used in a similar fashion to generate a deactivation or shutdown signal to transition the electronic device to a sleep mode. For example, a received pulse train can be detected by the rectifier and adjusted by the Schmidt trigger, the pulse characteristics can be measured by the pulse timer circuit and the counter used to count the number of valid pulses to detect a valid shutdown signal. In some embodiments, the shutdown signal can be the same as or different from the startup signal. If a valid shutdown signal is received at the antenna and detected by starter circuit 128, starter circuit 128 can generate the appropriate signal to transition the transceiver (or the electronic device) into the sleep mode.

Figure 6:
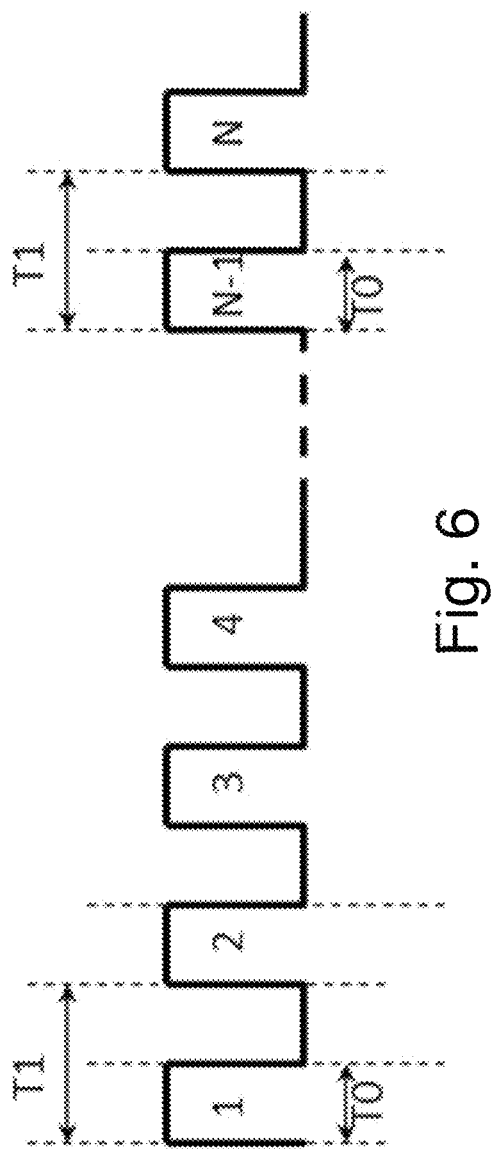
FIG. 6 is a diagram illustrating an example pulse sequence in accordance with one embodiment of the technology described herein.

The startup circuitry can be configured to consume very low power until it is activated and in various embodiments requires minimal over-head circuitry. Because power consumption is important, the startup circuitry can be configured to use a simple pulse scheme for the startup signal such as, for example, an on-off keying modulation (OOK). FIG. 6 is a diagram illustrating an example pulse sequence in accordance with one embodiment of the technology described herein. In this example, the number of pulses (N), the period (T1) and the duty cycle (T0) of the pulse determines the desired startup sequence as shown in FIG. 6. The pulse timer generates the reset pulse for the counter when the timing of any of these parameters is outside of a predefined acceptable range. When a sequence of N pulses of the appropriate parameters has been received, the counter generates the startup sequence to enable the transceiver.

Figure 7:
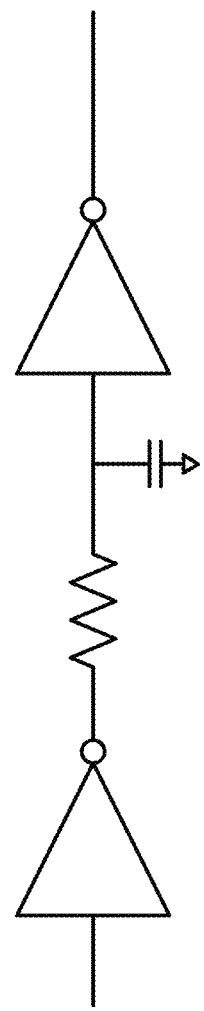
FIG. 7 is a diagram illustrating a simplified example of a pulse timing circuit in accordance with one embodiment of the technology described herein.

FIG. 7 is a diagram illustrating a simplified example of a pulse timing circuit in accordance with one embodiment of the technology described herein. In various embodiments, a separate circuit is provided for each time constant T0, T1 and N.T1 to generate the appropriate reset pulse.

Figure 8:
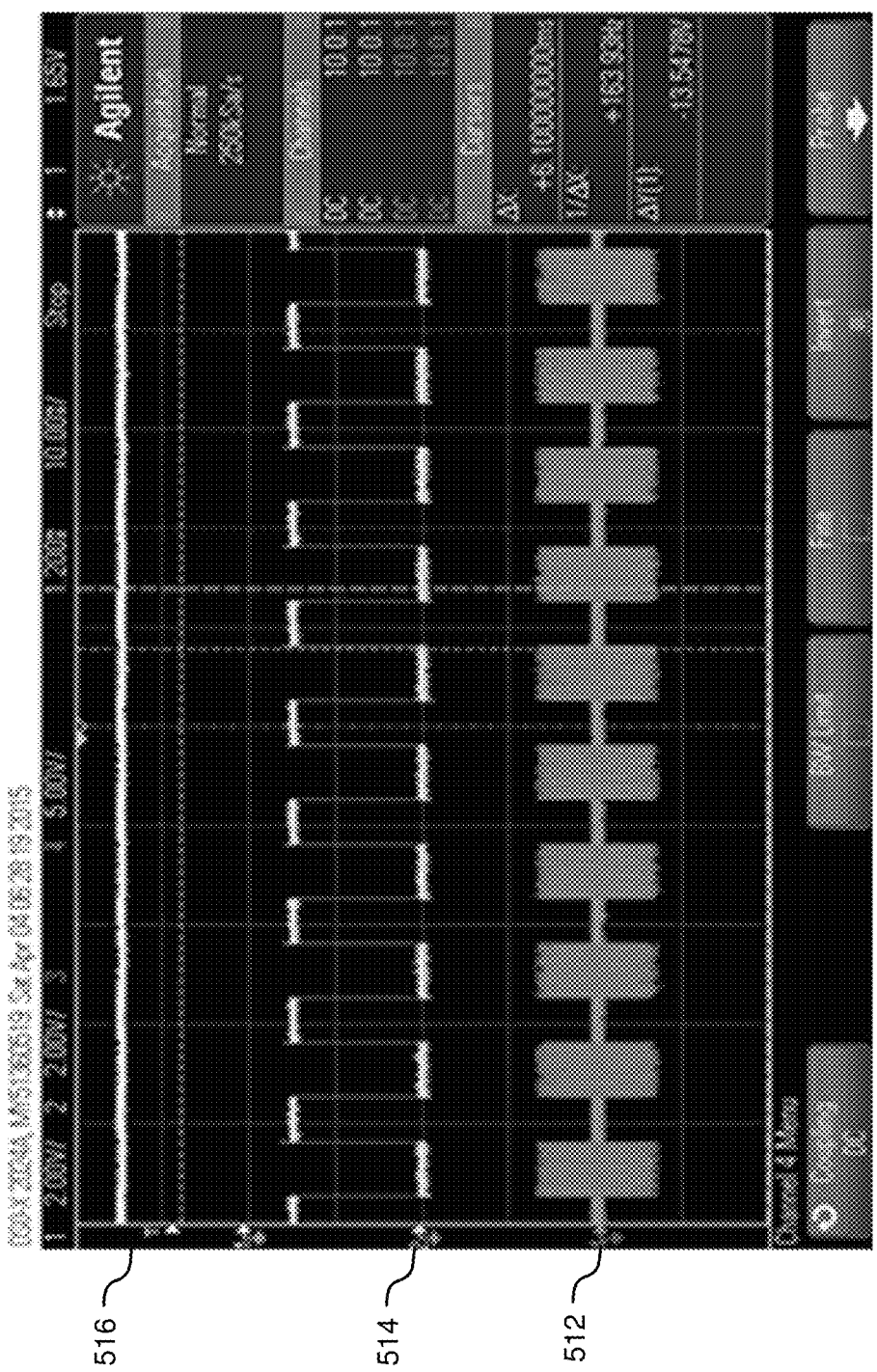
FIGS. 8 and 9 are diagrams illustrating screen captures of a lab measurement of a startup wave form, count pulse and reset signal in accordance with one embodiment of the technology described herein.
Figure 9:
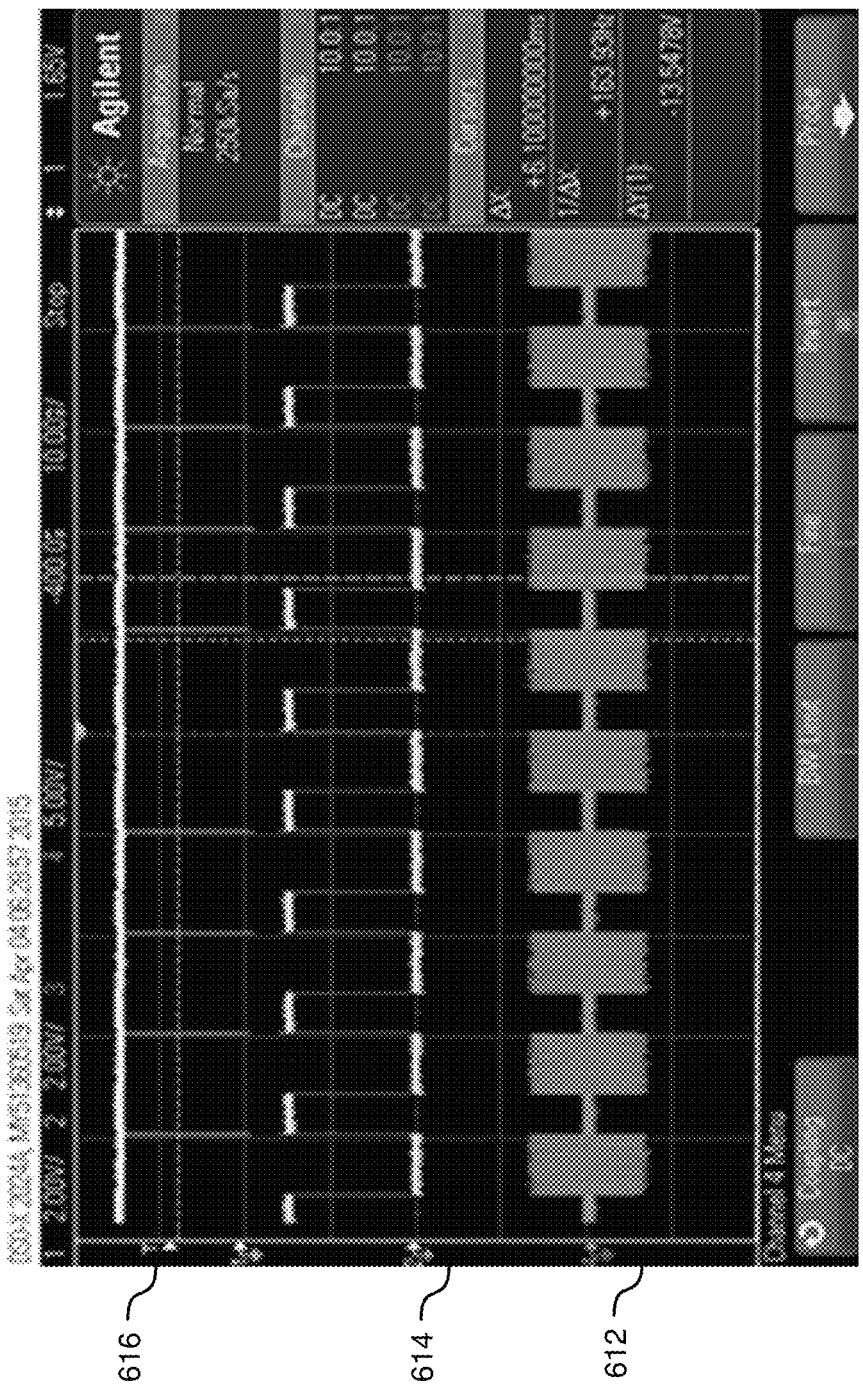

FIGS. 8 and 9 are diagrams illustrating screen captures of a lab measurement of a startup wave form, count pulse and reset signal in accordance with one embodiment of the technology described herein. As illustrated in the example of FIG. 8, the circuit receives signal 512, which may or may not be a valid startup signal. The signal 512 is detected and the Schmidt trigger produces pulses 514 as shown in the center of the screen. Because in this example the pulses are valid, reset signal 516 is not triggered. In contrast, in the example of FIG. 9, signal 612 is detected and the Schmidt trigger produces pulses 614. However, because in this example there are pulses that don't meet the appropriate parameters (e.g. the duty cycle is too low) and a reset pulse is generated at reset signal 616 for each of those pulses. Where one pulse does meet those parameters, the reset pulse is not generated as seen at the top center of the screen.

Although the example described above uses a predetermined number of pulses of a predefined pulse width and duty cycle, any of a variety of different keying schemes can be used to help ensure that the electronic device is not inadvertently or maliciously triggered. For example, different coding or modulation schemes can be used to provide the keying. Furthermore, different electronic devices can use different keys such that one particular device among a group of devices in close proximity can be selectively activated by transmitting the designated key to that device. This can help to ensure that only the selected device is triggered and that the unselected devices are not inadvertently triggered at the same time. In further embodiments, a power-off or shutdown sequence can also be provided to allow a similar mechanism to power down the device and return it to the sleep mode.

In various embodiments, the starter circuit is simple enough so that it does not add any significant area penalty nor does it have a significant impact on the overall size of the electronic device with which it is being implemented. Hence reusing any of the existing transceiver components, such as the receiver and the antenna as described in the examples above, contributes to the attractiveness of the solution. The antenna of the electronic device that is used for either the uplink or downlink communication can also be used to receive the startup sequence as described in the examples above. Accordingly, the carrier frequency of the startup sequence is the same as or similar to that of the communication link to enable the antenna and the receiver to adequately receive the startup signal. Although setting a startup sequence carrier frequency exactly identical to that of the communication link would be ideal, the carrier frequency of the startup sequence does not need to be that precise in all applications. Indeed, it may be approximately the same as the frequency of the communication link such that the carrier frequency of the startup sequence is at least close enough to the carrier frequency of the communication link for the electronic device such that pulses in the startup sequence can be adequately detected and counted to enable startup.

In order for the startup sequence to not interfere with the normal operation of the communication link, the signal levels for the starter circuit are higher than the normal operation of the communication link. This is possible since the received signal of the implantable/ingestible component has the additional loss of human tissue and hence is weaker than the startup signal. However the transceiver input stage should be able to handle this signal level without breakdown. Additionally the input stage of the starter should be designed such that it does not respond to typical signal levels of the communication link.

The various circuits or blocks described herein may be implemented utilizing any form of hardware, software, or a combination thereof. A circuit may include, for example, one or more processors, controllers, central processing units, ASICs, PLAs, PALs, PLDs, CPLDs, FPGAs, logical components, or other mechanism or device that manipulates or operates on signals, whether analog or digital, based on hard coding, configuration or wiring of the circuitry, the execution of operational instructions, or a combination thereof.

The circuit may further include, memory (separate, integrated or embedded from the one or more processors), which may be include one or more memory devices. Such a memory device may include, for example, one or a combination of memory types such as read-only memory, random access memory, volatile and non-volatile memory, static memory, dynamic memory, flash memory, cache memory, or other information storage device, whether magnetic, acoustic, optical or otherwise.

The circuits described herein might be implemented as discrete circuits or modules or the functions or two or more of the circuits described can be combined. For example, even though various features or elements of functionality may be individually described or claimed as separate subsystems or blocks, one of ordinary skill in the art will understand that these features and functionality can be shared among one or more common software and hardware elements, and such description shall not require or imply that separate hardware or software components are used to implement such features or functionality.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A starter circuit for an electronic device, comprising;
   a rectifier circuit comprising an input coupled to an antenna;
   a Schmidt trigger comprising an input coupled to receive a rectified signal from the rectifier circuit;
   a pulse timer circuit coupled to receive pulses from the Schmidt trigger and configured to measure pulse characteristics to determine whether the pulses are part of a valid startup sequence and to generate a reset signal if the pulses are not part of a valid startup sequence; and
   a counter having first and second inputs coupled to outputs of the pulse timer circuit, the counter configured to output a signal to initiate power-on of a component of the electronic device when its count value reaches a predetermined value,
   wherein the starter circuit sends the signal to initiate power-on of the component of the electronic device only when: (i) a power level of a signal received by the rectifier circuit from the antenna is equal to or greater than a predetermined power level that is greater than a power level of communication signals received by the electronic device, and (ii) the signal received by the rectifier circuit include a startup sequence that is a predetermined startup sequence indicating that the component of the electronic device is to switch from a sleep mode to an active mode.

2. The starter circuit of claim 1, wherein the pulse characteristics comprise pulse width and period.

3. The starter circuit of claim 1, wherein the valid startup sequence is an OOK modulated signal.

4. The starter circuit of claim 1, wherein measuring the pulse characteristics to determine whether the pulses are part of the valid startup sequence comprises measuring timing parameters of the pulses to determine whether the pulses meet predetermined timing parameter characteristics.

5. The starter circuit of claim 4, wherein the timing parameters comprise a pulse width and a period of the pulses.

6. The starter circuit of claim 1, wherein the rectifier circuit outputs the rectified signal only if the power level of the signal received by the rectifier circuit from the antenna is equal to or greater than the predetermined power level.

7. The starter circuit of claim 1, wherein the starter circuit is configured to send a shutdown signal to the electronic device to cause the electronic component to switch to a sleep mode,
   wherein the starter circuit sends the shutdown signal to the electronic device only when: (i) a power level of a signal received by the rectifier circuit from the antenna is equal to or greater than a predetermined power level, and (ii) the signal received by the rectifier circuit includes a shutdown sequence that is a predetermined shutdown sequence indicating that the component of the electronic device is to switch from an active mode to the sleep mode.

8. A starter circuit for an electronic device, comprising;
   a rectifier circuit comprising an input coupled to an antenna;
   a Schmidt trigger comprising an input coupled to receive a rectified signal from the rectifier circuit;
   a pulse timer circuit coupled to receive pulses from the Schmidt trigger and configured to measure pulse characteristics to determine whether the pulses are part of a valid startup sequence and to generate a reset signal if the pulses are not part of a valid startup sequence; and
   a counter having first and second inputs coupled to outputs of the pulse timer circuit, the counter configured to output a signal to initiate power-on of a component of the electronic device when its count value reaches a predetermined value, wherein the starter circuit is configured to send a shutdown signal to the electronic device to cause the electronic component to switch to a sleep mode;

wherein the starter circuit sends the shutdown signal to the electronic device only when: (i) a power level of a signal received by the rectifier circuit from the antenna is equal to or greater than a predetermined power level, and (ii) the signal received by the rectifier circuit includes a shutdown sequence that is a predetermined shutdown sequence indicating that the transceiver component of the electronic device is to switch from an active mode to the sleep mode.

9. The starter circuit of claim 1, wherein the electronic device comprises a wireless ingestible endoscope, wherein the component of the electronic device comprises a transceiver.

10. The starter circuit of claim 1, wherein the starter circuit consumes a leakage current in the sleep mode that is less than a leakage current the component of the electronic device consumes in the active mode.

11. The starter circuit of claim 1, wherein the rectifier circuit comprises a power detector.

12. A wireless ingestible endoscopy system, comprising:
an endoscopy data terminal;
a wireless ingestible endoscope comprising:
  an image sensor;
  a communication transceiver coupled to receive images from the image sensor and configured to send images to the endoscopy data terminal;
  a starter circuit, comprising:
    a rectifier circuit comprising an input coupled to an antenna;
    a Schmidt trigger comprising an input coupled to receive a rectified signal from the rectifier circuit;
    a pulse timer circuit coupled to receive pulses from the Schmidt trigger and configured to measure pulse characteristics to determine whether the pulses are part of a valid startup sequence and to generate a reset signal if the pulses are not part of a valid startup sequence; and
    a counter having first and second inputs coupled to outputs of the pulse timer circuit, the counter configured to output a signal to initiate power on of the transceiver when the counter's count value reaches a predetermined value,
  wherein the starter circuit sends the signal to initiate power on of the transceiver only when: (i) a power level of a signal received by the rectifier circuit from the antenna is equal to or greater than a predetermined power level that is greater than a power level of communication signals received by the transceiver, and (ii) the signal received by the rectifier circuit includes a startup sequence that is a predetermined startup sequence indicating that the transceiver is to switch from a sleep mode to an active mode.

13. The system of claim 12, wherein the system further comprises an external antenna, and wherein the images are sent from the communication transceiver to the endoscopy data terminal via the external antenna.

14. The system of claim 12, wherein the endoscopy data terminal comprises a data recorder or workstation.

15. The system of claim 12, wherein measuring the pulse characteristics to determine whether the pulses are part of the valid startup sequence comprises measuring timing parameters of the pulses to determine whether the pulses meet predetermined timing parameter characteristics.

16. The system of claim 15, wherein the timing parameters comprise a pulse width and a period of the pulses.

17. The system of claim 12, wherein the rectifier circuit outputs the rectified signal only if the power level of the signal received by the rectifier circuit from the antenna is equal to or greater than the predetermined power level.

18. The system of claim 12, wherein the starter circuit is configured to send a shutdown signal to the transceiver to cause the transceiver to switch to the sleep mode.

19. The system of claim 18, wherein the starter circuit sends the shutdown signal to the transceiver only when: (i) the power level of the signal received by the rectifier circuit from the antenna is equal to or greater than the predetermined power level, and (ii) the signal received by the rectifier circuit includes a shutdown sequence that is a predetermined shutdown sequence indicating that the transceiver is to switch from the active mode to the sleep mode.

20. The system of claim 12, wherein the starter circuit consumes a leakage current in the sleep mode that is less than a leakage current the transceiver consumes in the active mode.

21. A radio communication device comprising:
an antenna;
a transceiver including an input coupled to receive signals from the antenna, the transceiver comprising an active mode and a sleep mode; and
an AC starter circuit including an input coupled to receive signals from the antenna and an output coupled to the transceiver, the AC starter circuit comprising a rectifier circuit coupled to receive the signals from the antenna and configured to generate a rectified radio signal only when a power level of the received signals is equal to or greater than a first predetermined power level;
wherein the AC starter circuit sends:
  an activation signal to the transceiver only when: (i) the power level of the received signal is equal to or greater than the first predetermined power level, which is greater than a power level of communication signals received by the transceiver, and (ii) the received signals include a startup sequence that is a predetermined startup sequence indicating that the transceiver is to switch from the sleep mode to the active mode; and wherein the AC starter circuit does not send the activation signal to the transceiver when the power level of the received signals is not equal to or greater than the first predetermined power level or when the startup sequence is not the predetermined startup sequence; or
  a shutdown signal to the transceiver only when: (i) the power level of the received signal is equal to or greater than the first predetermined power level, which is greater than a power level of communication signals received by the transceiver, and (ii) the received signals include a shutdown sequence that is a predetermined shutdown sequence indicating that the transceiver is to switch from the active mode to the sleep mode; and wherein the AC starter circuit does not send the shutdown signal to the transceiver when the power level of the received signals is not equal to or greater than the first predetermined power level or when the shutdown sequence is not the predetermined shutdown sequence;
wherein the transceiver switches its operation mode from the sleep mode to the active mode when the transceiver in the sleep mode receives the activation signal from the AC starter circuit; or wherein the transceiver switches its operational mode from the active mode to the sleep mode when the transceiver in the active mode receives the shutdown signal from the AC starter circuit;

wherein the transceiver in the active mode decodes a radio signal received by the antenna, when a power level of the radio signal is equal to or greater than a second predetermined power level; and wherein the AC starter circuit consumes a leakage current less than a leakage current which the transceiver consumes in the active mode.

22. The radio communication device of claim 21, wherein the second predetermined power level is within a dynamic range in which the transceiver is operable; and the first predetermined power level is more than double the second predetermined power level.

23. The radio communication device of claim 21, wherein the AC starter circuit is configured to send the shutdown signal to the transceiver to cause the transceiver to switch to the sleep mode.

24. The radio communication device of claim 21, wherein the AC starter circuit is configured to send the activation signal to the transceiver to cause the transceiver to switch to the active mode.

* * * * *